(12) United States Patent
Ho

(10) Patent No.: US 8,354,554 B2
(45) Date of Patent: Jan. 15, 2013

(54) PROCESS FOR PREPARING ORGANOMETALLOIDS

(75) Inventor: Chun Yu Ho, Laguna (CN)

(73) Assignee: The Chinese University of HongKong, HongKong (CN)

( * ) Notice: Subject to any disclaimer, the term of this patent is extended or adjusted under 35 U.S.C. 154(b) by 267 days.

(21) Appl. No.: 12/887,981

(22) Filed: Sep. 22, 2010

(65) Prior Publication Data

US 2012/0071681 A1    Mar. 22, 2012

(51) Int. Cl.
*C07F 7/04* (2006.01)
*C07F 7/08* (2006.01)

(52) U.S. Cl. ...................... 556/466; 556/489

(58) Field of Classification Search .................. 556/466, 556/489
See application file for complete search history.

(56) References Cited

OTHER PUBLICATIONS

Hosomi et al., Organosilicon chemistry, Tetrahedron Letters (1990), 31(43), Chemical abstract DN: 114:102165.*

* cited by examiner

*Primary Examiner* — Jafar Parsa
(74) *Attorney, Agent, or Firm* — Ping Wang; Andrews Kurth, LLP

(57) ABSTRACT

Disclosed are a process for preparing organometalloids functionalized with an unsymmetrical 1,1-disubstituted alkene, and compounds prepared therewith.

19 Claims, 16 Drawing Sheets

PROCESS FOR PREPARING ORGANOMETALLOIDS

FIELD

The present application is directed to organic synthesis chemistry, in particular to a process for preparing organometalloids.

BACKGROUND

Synthesis of new organometalloids, particularly organometalloids functionalized with an unsymmetrical 1,1-disubstituted alkene is one of the most important aspects in organic synthesis chemistry, since organometalloids have been found in broad applications due to their unique properties such as electrical conductivity, magnetism, and chemical reactivity.

Methods for preparing organometalloids functionalized with an unsymmetrical 1,1-disubstituted alkene in the art may generally rely on expensive starting materials. Most of the methods are stoichiometric in nature or suffer from significant waste disposal problems in a large scale (e.g. phosphine oxide, arylsulfonate, titanium/aluminum salt, silyl ether and halides) or substrate availability.

There are only very limited availability and choices of 1,1-disubstituted alkenes and homoallylmetalloids on the market, mainly constrained by the availability of natural products, petroleum cracking and selective dehydrogenation of several alkanes. According to the Sigma-Aldrich product catalogue, there are only around twenty 1,1-disubstituted alkenes available in stock (a very low amount compared to aromatic alkenes and alpha-alkenes, http://www.sigmaaldrich.com/chemistry/chemistry-products.html?TablePage-16274429).

Synthesis of organometalloids functionalized with an unsymmetrical 1,1-disubstituted alkene from vinylmetalloids and α-olefins may suffer from side reactions such as olefin isomerization/oligomerization, self-dimerization, hydrogenative dimerization, dehydrogenative silylation, silylative coupling, and Hiyama coupling, resulting in a mixture of regioisomers and a significant amount of toxic transition metal waste.

SUMMARY

The present application converts relatively unreactive alkenes to more reactive ones. With this technology, desired products can be provided with conventional olefins through organometalloids functionalization.

In one aspect, the present application provides a process for preparing a compound of formula (III), comprising reacting a compound of formula (I) with a compound of formula (II) in the presence of a transition metal catalyst or a precursor thereof,

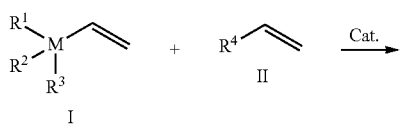

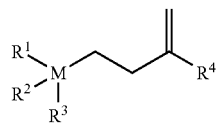

wherein,
M is a metalloid,
$R^1$, $R^2$ and $R^3$ are each independently selected from the group consisting of H, alkyl, alkenyl, aryl, arylalkyl, hydroxyl, alkoxyl, aroxyl, halogen, amino, alkylamino, arylamino, mercapto, alkylthio and arylthio, and
$R^4$ is alkyl, cycloalkyl, aryl or arylalkyl.

In another aspect, the present application is directed to a compound of formula (III)

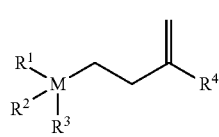

wherein,
M is a metalloid,
$R^1$, $R^2$ and $R^3$ are each independently selected from the group consisting of H, alkyl, alkenyl, aryl, arylalkyl, hydroxyl, alkoxyl, aroxyl, halogen, amino, alkylamino, arylamino, mercapto, alkylthio and arylthio, and
$R^4$ is alkyl, cycloalkyl, aryl or arylalkyl.

BRIEF DESCRIPTION OF THE FIGURES

FIGS. 1A and 1B show $^1$H- and $^{13}$C-NMR spectra of the compound 3a.

DETAILED DESCRIPTION

Figure 1A:
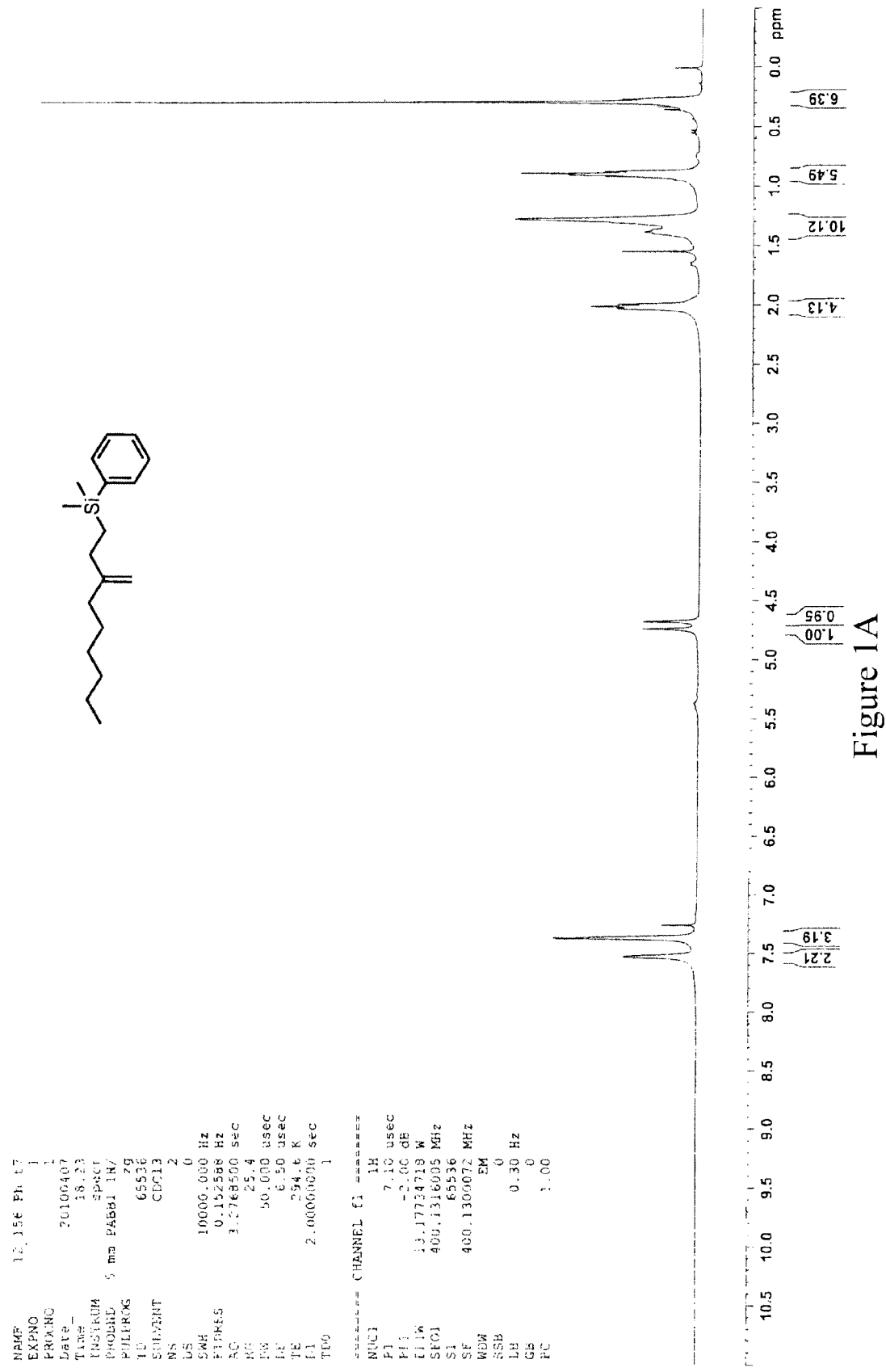

The present application is to change the typically observed reactivity pattern of vinylsilane and α-olefin towards transition metal complex, and to control the regioselectivity of a carbon-carbon bond forming reaction between two alkenes, strongly favoring the production of 1,1-disubstituted alkenes in a head-to-tail fashion.

The present application is also to provide a cost effective and environmentally friendly way to fulfill the increasing demand of both organometalloids and 1,1-disubstituted alkenes.

DEFINITIONS

In the following description, certain specific details are included to facilitate a thorough understanding of various disclosed embodiments. One skilled in the relevant art, however, will recognize that embodiments may be practiced without one or more of these specific details, or with other methods, components, materials, etc.

Unless the context requires otherwise, throughout the specification and claims which follow, the word "comprise" and variations thereof, such as "comprises" and "comprising", are to be construed in an open, inclusive sense, which is as "including, but not limited to."

Reference throughout this specification to "one embodiment," or "an embodiment", or "in another embodiment," or "some embodiments," or "in some embodiments" means that a particular referent feature, structure, or characteristic described in connection with the embodiment is included in at least one embodiment. Thus, the appearance of the phrases "in one embodiment," or "in an embodiment," or "in another embodiment," or "in some embodiments" in various places throughout this specification are not necessarily all referring to the same embodiment. Furthermore, the particular features, structures, or characteristics may be combined in any suitable manner in one or more embodiments.

It should be noted that, as used in this specification and the appended claims, the singular forms "a," "an," and "the" include plural referents unless the content clearly indicates otherwise. In the present application, the use of "or" means "and/or" unless specifically stated otherwise.

Certain chemical groups named herein are preceded by a shorthand notation indicating the total number of carbon atoms that are to be found in the indicated chemical group. For example, $C_7$-$C_{12}$ alkyl describes an alkyl group, as defined below, having a total of 7 to 12 carbon atoms. The total number of carbons in the shorthand notation does not include carbons that may exist in substituents of the group described.

As used herein, "$C_m$ to $C_n$" or "$C_{m\ to\ n}$" in which "in" and "n" are integers refers to the number of carbon atoms in an alkyl or alkenyl group or the number of carbon atoms in the ring of a cycloalkyl or cycloalkenyl group. That is, the alkyl, alkenyl, ring of the cycloalkyl or ring of the cycloalkenyl can contain from "m" to "n", inclusively, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "m" and "n" are designated with regard to an alkyl, alkenyl, cycloalkyl or cycloalkenyl group, the broadest range described in these definitions is to be assumed.

Accordingly, as used in the specification and appended claims, unless specified to the contrary, the following terms have the meaning indicated:

The term "alkyl" as used herein alone or as part of a group means any unbranched or branched, substituted or unsubstituted, saturated hydrocarbon group. The alkyl moiety may be a branched or straight chain. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, the substituent group may be one or more groups individually and independently selected from substituted or unsubstituted cycloalkyl, substituted or unsubstituted cycloalkenyl, substituted or unsubstituted aryl, substituted or unsubstituted heteroaryl, substituted or unsubstituted heteroaryloxy, heterocyclyl, heterocyclyloxy, heteroalicyclyl, hydroxy, substituted or unsubstituted alkoxy, substituted or unsubstituted aryloxy, acyl, thiol, substituted or unsubstituted thioalkoxy, alkylthio, arylthio, cyano, halo, carbonyl, thiocarbonyl, acylalkyl, acylamino, acyloxy, aminoacyl, aminoacyloxy, oxyacylamino, keto, thioketo, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and substituted or unsubstituted amino, including mono- and di-substituted amino groups, and the protected derivatives thereof, hydroxyamino, alkoxyamino, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl. Typical alkyl groups include, but are in no way limited to, methyl, ethyl, propyl, isopropyl, butyl, isobutyl, tertiary butyl, pentyl, hexyl, and the like.

The term "alkenyl" as used herein alone or as part of a group refers to a straight or branched hydrocarbon chain group consisting solely of carbon and hydrogen atoms, containing at least one double bond, having from two to twelve carbon atoms, preferably two to eight carbon atoms and which is attached to the rest of the molecule by a single bond, e.g., ethenyl, propenyl, butenyl, pentenyl, penta-1,4-dienyl, and the like.

The term "cycloalkyl" as used herein alone or as part of a group refers to a completely saturated (no double bonds) mono- or multi-cyclic hydrocarbon ring system. When composed of two or more rings, the rings may be joined together in a fused, bridged or spiro-connected fashion. Cycloalkyl groups of the present application may range from $C_3$ to $C_{10}$. In other embodiments, it may range from $C_3$ to $C_6$. A cycloalkyl group may be unsubstituted or substituted. Typical cycloalkyl groups include, but are not limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated.

The term "cycloalkenyl" as used herein alone or as part of a group refers to a cycloalkyl group that contains one or more double bonds in the ring although, if there is more than one, they cannot form a fully delocalized pi-electron system in the ring (otherwise the group would be "aryl", as defined herein). When composed of two or more rings, the rings may be connected together in a fused, bridged or spiro-connected fashion. A cycloalkenyl group of the present application may be unsubstituted or substituted. When substituted, the substituent(s) may be an alkyl or selected from the groups disclosed above with regard to alkyl group substitution unless otherwise indicated. The number of carbon atoms in the cycloalkenyl may be in the range of 3 to 10.

The term "carbonyl" as used herein alone or as part of a group refers to the group —(C=O).

The term "alkoxy" as used herein alone or as part of a group refers to any unbranched, or branched, substituted or unsubstituted, saturated or unsaturated ether, with $C_1$-$C_6$ unbranched, saturated, unsubstituted ethers being preferred, with methoxy and ethoxy being more preferred.

The term "alkylamino" as used herein alone or as part of a group refers to the group —NH-alkyl.

The term "halo" or "halogen" as used herein alone or as part of a group refers to bromo, chloro, fluoro or iodo.

The term "heterocyclyl" as used herein alone or as part of a group is intended to mean three-, four-, five-, six-, seven-, and eight- or more membered rings wherein carbon atoms together with from 1 to 3 heteroatoms constitute the ring. A heterocyclyl can optionally contain one or more unsaturated bonds situated in such a way, however, that an aromatic pi-electron system does not arise. The heteroatoms are independently selected from oxygen, sulfur, and nitrogen.

A heterocyclyl can further contain one or more carbonyl or thiocarbonyl functionalities, so as to make the definition include oxo-systems and thio-systems such as lactams, lactones, cyclic imides, cyclic thioimides, cyclic carbamates, and the like.

Heterocyclyl rings can optionally be fused ring systems containing two or more rings wherein at least one atom is shared between two or more rings to form bicyclic or tricyclic structures. In some embodiments, such fused ring systems are formed by a bridging moiety between two atoms of a heterocyclyl.

Heterocyclyl rings can optionally also be fused to aryl rings, such that the definition includes bicyclic structures. Typically such fused heterocyclyl groups share one bond with an optionally substituted benzene ring. Examples of benzo-fused heterocyclyl groups include, but are not limited to, benzimidazolidinone, tetrahydroquinoline, and methylenedioxybenzene ring structures.

Some examples of "heterocyclyls" include, but are not limited to, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, 1,3-oxathiolane, and an azabicyclo system such as azabicyclo[3.2.1]octyl (tropane). Binding to the heterocycle can be at the position of a heteroatom or via a carbon atom of the heterocycle, or, for benzo-fused derivatives, via a carbon of the benzenoid ring.

The term "aromatic" as used herein refers to an aromatic group which has at least one ring having a conjugated pi electron system and includes both carbocyclic aryl (e.g., phenyl) and heterocyclic aryl groups (e.g., pyridine). The term includes monocyclic or fused-ring polycyclic (i.e., rings which share adjacent pairs of carbon atoms) groups.

The term "carbocyclic" as used herein, refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" as used herein, refers to an aromatic group which contains at least one heterocyclic ring.

The term "aryl" as used herein alone or as part of a group is intended to mean a carbocyclic aromatic ring or ring system. Moreover, the term "aryl" includes fused ring systems wherein at least two aryl rings, or at least one aryl and at least one $C_{3-8}$-cycloalkyl share at least one chemical bond. Some examples of "aryl" rings include optionally substituted phenyl, naphthalenyl, phenanthrenyl, anthracenyl, tetralinyl, fluorenyl, indenyl, and indanyl.

The term "aryl" relates to aromatic, including, for example, benzenoid groups, connected via one of the ring-forming carbon atoms, and optionally carrying one or more substituents selected from heterocyclyl, heteroaryl, halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. The aryl group can be substituted at the para and/or meta positions. In other embodiments, the aryl group can be substituted at the ortho position. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, trifluoromethylphenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

The term "arylalkyl" or "aralkyl" as used herein alone or as part of a group which are used synonymously and interchangeably refers to an aryl group covalently bonded to an alkyl group, as defined herein. A "phenylalkyl" is a species of an aralkyl group, and refers to a phenyl ring covalently bonded to an alkyl group as defined herein. Examples of phenylalkyl groups include, but are not limited to, benzyl, 2-phenylethyl, 1-phenylpropyl, 4-phenylhexyl, 3-phenylamyl and 3-phenyl-2-methylpropyl. Presently preferred phenylalkyl groups are those wherein the phenyl group is covalently bonded to one of the presently preferred alkyl groups. A phenyl alkyl group of the present application may be unsubstituted or substituted. Examples of substituted phenylalkyl groups include, but are not limited to, 2-phenyl-1-chloroethyl, 2-(4-methoxyphenyl)ethyl, 4-(2,6-dihydroxyphenyl)hexyl, 2-(5-cyano-3-methoxyphenyl)pentyl, 3-(2,6-dimethylphenyl)propyl, 4-chloro-3-aminobenzyl, 6-(4-methoxyphenyl)-3-carboxy(n-hexyl), 5-(4-aminomethylphenyl)-3-(aminomethyl)pentyl and 5-phenyl-3-oxo-pent-1-yl.

The term "heteroaryl" as used herein alone or as part of a group is intended to mean a heterocyclic aromatic group where one or more carbon atoms in an aromatic ring have been replaced with one or more heteroatoms selected from the group comprising nitrogen, sulfur, and oxygen.

Furthermore, in the present context, the term "heteroaryl" comprises fused ring systems wherein at least one aryl ring and at least one heteroaryl ring, at least two heteroaryl rings, at least one heteroaryl ring and at least one heterocyclyl ring, or at least one heteroaryl ring and at least one cycloalkyl ring share at least one chemical bond.

The term "heteroaryl" is understood to relate to aromatic, $C_{3-8}$ cyclic groups further containing one oxygen or sulfur atom or up to four nitrogen atoms, or a combination of one oxygen or sulfur atom with up to two nitrogen atoms, and their substituted as well as benzo- and pyrido-fused derivatives, for example, connected via one of the ring-forming carbon atoms. Heteroaryl groups can carry one or more substituents selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. In some embodiments, heteroaryl groups can be five- and six-membered aromatic heterocyclic systems carrying 0, 1, or 2 substituents, which can be the same as or different from one another, selected from the list above.

Representative examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

The term "phenyl" as used herein alone or as part of a group refers to a six-membered aryl group. A phenyl group may be unsubstituted or substituted. When substituted the substituent(s) is(are) one or more, preferably one or two, group(s) independently selected from the group consisting of halogen, hydroxy, protected hydroxy, cyano, nitro, alkyl, alkoxy, acyl, acyloxy, carboxy, protected carboxy, carboxymethyl, protected carboxymethyl, hydroxymethyl, protected hydroxymethyl, —NRR', carboxamide, protected carboxamide, N-alkylcarboxamide, protected N-alkylcarboxamide, N,N-dialkylcarboxamide, trifluoromethyl, N-alkylsulfonylamino, N-(phenylsulfonyl)amino and phenyl (resulting in the formation of a biphenyl group).

Examples of substituted phenyl groups include, but are not limited to, 2-, 3- or 4-chlorophenyl, 2,6-dichlorophenyl, 2,5-dichlorophenyl, 3,4-dichlorophenyl, 2-, 3- or 4-bromophenyl, 3,4-dibromophenyl, 3-chloro-4-fluorophenyl, 2-, 3- or 4-fluorophenyl, 2-, 3- or 4-hydroxyphenyl, 2,4-dihydroxyphenyl, the protected-hydroxy derivatives thereof, 2-, 3- or 4-nitrophenyl; 2-, 3- or 4-cyanophenyl, 2-, 3- or 4-methylphenyl, 2,4-dimethylphenyl, 2-, 3- or 4-(iso-propyl)phenyl, 2-, 3- or 4-ethylphenyl, 2-, 3- or 4-(n-propyl)phenyl, 2,6-dimethoxyphenyl, 2-, 3- or 4-methoxyphenyl, 2-, 3- or 4-ethoxyphenyl, 2-, 3- or 4-(isopropoxy)phenyl, 2-, 3- or 4-(t-butoxy)phenyl, 3-ethoxy-4-methoxyphenyl, 2-, 3- or 4-trifluoromethylphenyl, 2-, 3- or 4-carboxyphenyl or 2,4-di(protected carboxy) phenyl, 2-, 3-, or 4-(protected hydroxymethyl)phenyl or 3,4-di(hydroxymethyl)phenyl, 2-, 3- or 4-(aminomethyl)phenyl or 2,4-(protected aminomethyl)phenyl, and 2-, 3- or 4-(N-(methylsulfonylamino))phenyl.

The term "mercapto" as used herein refers to a group of formula "—SH".

The term "alkylthio" as used herein alone or as part of a group refers to an "alkyl-S—" group, with alkyl as defined above. Examples of alkylthio group include, but are not limited to, methylthio, ethylthio, n-propylthio, isopropylthio, n-butylthio and t-butylthio.

The term "arylthio" as used herein alone or as part of a group refers to an "aryl-S—" group, with aryl as defined above. Examples of arylthio group include, but are not limited to, phenylthio, naphthylthio, and anthracylthio.

The term "alkylsulfinyl" as used herein alone or as part of a group refers to an "alkyl-$SO_2$—" group, with alkyl as defined above. Examples of alkylsulfinyl groups include, but are not limited to, methylsulfinyl, ethylsulfinyl, n-propylsulfinyl, isopropylsulfinyl, n-butylsulfinyl and sec-butylsulfinyl.

The term "alkylsulfonyl" as used herein alone or as part of a group refers to an "alkyl-$SO_2$—" group. Examples of alkylsulfonyl groups include, but are not limited to, methylsulfonyl, ethylsulfonyl, n-propylsulfonyl, isopropylsulfonyl, n-butylsulfonyl, and t-butylsulfonyl.

The terms "phenylthio", "phenylsulfinyl", and "phenylsulfonyl" as used herein alone or as part of a group refer to a "phenyl-S—", "phenyl-SO—", and "phenyl-$SO_2$—" group, phenyl as defined herein.

The term "amine" as used herein refers to a compound that comprises an amino group. The term "amino" as used herein alone or as part of a group refers to the —$NH_2$ radical.

The term "cyano" as used herein alone or as part of a group refers to the —CN radical.

The term "hydroxy" as used herein alone or as part of a group refers to the —OH radical.

The term "imine" as used herein refers to a compound that comprises an imino group. The term "imino" as used herein alone or as part of a group refers to the =NH substituent.

The term "nitro" as used herein alone or as part of a group refers to the —$NO_2$ radical.

The term "oxo" as used herein alone or as part of a group refers to the =O substituent.

The term "trifluoromethyl" as used herein alone or as part of a group refers to the —$CF_3$ radical.

The term "optional" or "optionally" as used herein means that the subsequently described event of circumstances may or may not occur, and that the description includes instances where said event or circumstance occurs and instances in which it does not.

Unless otherwise indicated, when a substituent is deemed to be "optionally substituted", it is meant that the substituent is a group that may be substituted with one or more group(s) individually and independently selected from morpholinoalkanoate, cycloalkyl, aryl, heteroaryl, heterocyclyl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof.

For example, "optionally substituted aryl" means that the aryl radical may or may not be substituted and that the description includes both substituted aryl radicals and aryl radicals having no substitution.

The term "transition metal" as used herein refers to any element in the d-block of the periodic table of the elements. This corresponds to groups 3 (IIIB) to 12 (IIB) on the periodic table.

The term "ligand" in chemistry generally refers to an atom, ion, or molecule that bonds to a central metal, generally involving formal donation of one or more of its electrons. The metal-ligand bonding ranges from covalent to more ionic.

The term "carbene(s)" as used herein refers to an organic molecule containing a carbon atom with six valence electrons and having the general formula RR'C:.

Metalloid, or semi metal, is a term used in chemistry when classifying the chemical elements. On the basis of their general physical and chemical properties, nearly every element in the periodic table can be termed either a metal or a nonmetal. However, a few elements are referred to as metalloids. There is no rigorous definition of the term, but the following properties are usually considered characteristic of metalloids: (1) metalloids often form amphoteric oxides; and (2) metalloids often behave as semiconductors (B, Si, Ge).

The following elements are generally considered metalloids: Boron (B), Silicon (Si), Germanium (Ge), Arsenic (As), Antimony (Sb), Tellurium (Te), and Polonium (Po).

In one aspect, the present application is directed to a process for preparing a compound of formula (III), comprising reacting a compound of formula (I) with a compound of formula (II) in the presence of a transition metal catalyst or a precursor thereof,

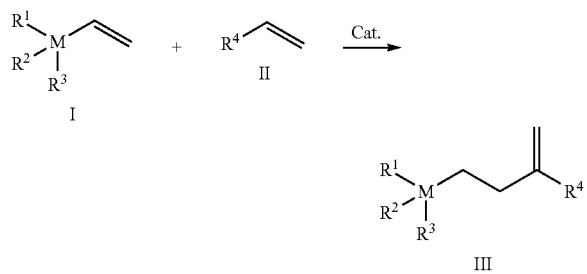

wherein,

M is a metalloid, $R^1$, $R^2$ and $R^3$ are each independently selected from the group consisting of H, alkyl, alkenyl, aryl, arylalkyl, hydroxyl, alkoxyl, aroxyl, halogen, amino, alkylamino, arylamino, mercapto, alkylthio and arylthio, and $R^4$ is alkyl, cycloalkyl, aryl or arylalkyl.

In some embodiments of the present application, M is Si.

In some embodiments of the present application, $R^1$, $R^2$ and $R^3$ are each independently selected from the group consisting of alkyl, aryl and alkoxyl.

Examples of the compounds of formula (I) that may be used in the present application include, but are not limited to trimethylvinylsilane, dimethylphenylvinylsilane, trimethoxyvinylsilane, triethoxyvinylsilane, triphenylvinylsilane, and the like.

Examples of the compounds of formula (II) that may be used in the present application include, but are not limited to 1-hexene/1-octene (straight chain monoene), vinylcyclohexane, 4-methyl-1-pentene (branched chain monoene), styrene, allylbenzene (aromatic alkenes) and their substituted derivatives thereof, more highly substituted alkenes, and the like.

The methods of the present application may be used to catalytically couple two different monosubstituted alkenes in head-to-tail manner to form a 1,1-disubstituted alkenes in one-pot. In some embodiments of the present application, the method is used to combine less reactive alkenes such as monoene or internal alkenes to build a more reactive one such as 1,1-disubstituted alkenes.

In some embodiments of the present application, the method is used to comprise two different alkenes in a single reaction chamber in the presence of a catalyst to form a homoallylmetalloid in nearly quantitative yield.

In one embodiment, the reaction may be intermolecular, i.e. the two reactants are not joined by a bond prior to the coupling reaction. In another embodiment, the reaction may be intramolecular.

The transition metal catalyst of the present application may include any catalytic transition metal and/or catalyst precursor as it is introduced into the reaction vessel and which may be, if needed, converted in situ into active form, as well as the active form of the catalyst which participates in the reaction. In some embodiments, the transition metal catalyst is provided in the reaction in a catalytic amount.

In some embodiments of the present application, the transition metal is selected from Groups 3 to 12 of the Periodic Table of Elements.

Exemplary transition metals that can be used in the present application include, but are not limited to, Scandium (Sc), Titanium (Ti), Vanadium (V), Chromium (Cr), Manganese (Mn), Iron (Fe), Cobalt (Co), Nickel (Ni), Copper (Cu), Zinc (Zn), Yttrium (Y), Zirconium (Zr), Niobium (Nb), Molybdenum (Mo), Technetium (Tc), Ruthenium (Ru), Rhodium (Rh), Palladium (Pd), Silver (Ag), Cadmium (Cd), Hafnium (Hf), Tantalum (Ta), Tungsten (W), Rhenium (Re), Osmium (Os), Iridium (Ir), Platinum (Pt), Gold (Au), Mercury (Hg), Rutherfordium (Rf), Dubnium (Db), Seaborgium (Sg), Bohrium (Bh), Hassium (Hs), Meitnerium (Mt), Darmstadtium (Ds), Roentgenium (Rg), and Ununbium (Uub).

In some embodiments of the present application, the transition metal is selected from Group 10 of the Periodic Table of Elements.

In some embodiments of the present application, the transition metal is selected from the group consisting of Nickel (Ni), Palladium (Pd) and Platinum (Pt). In some embodiments of the present application, the transition metal is Nickel (Ni).

The catalysts of the present application may also include heterogeneous catalysts that containing different forms of these above elements.

Ligands on the metal catalyst may include chelating ligands, such as (heterocyclic) carbene derivatives, and/or biscarbenes, bisheterocyclic carbenes, phosphines, amines, imines, arsines and derivatives thereof, including hybrids of the above.

In some embodiments of the present application, the ligand or metal bears a weakly or non-nucleophilic stabilizing ion, including but not limited to halogen, sulfonates, and phosphonates. Weakly or non-nucleophilic stabilizing ions are preferred to avoid complicating side reaction of the counter ion, for example, attacking or adding to the electrophilic center of the substrates.

Exemplary amines that can be used in the present application include, but are not limited to, aliphatic amines, and aromatic amines. Exemplary aliphatic amines that can be used in the present application include, but are not limited to, primary amines, secondary amines, and tertiary amines. Exemplary aliphatic amines that can be used in the present application include, but are not limited to, methylamine, ethanolamine, dimethylamine, methylethanolamine, trimethylamine, aziridine, piperidine, N-methylpiperidine, and the like. Exemplary aromatic amines that can be used in the present application include, but are not limited to, aniline, o-toluidine, 2,4,6-trimethylaniline, anisidine, 3-trifluoromethylaniline, and the like.

In some embodiments of the present application, additional ligands may be included in the catalyst to obtain a stable complex.

The ligand can be added to the reaction mixture in the form of a metal complex, or added as separate reagent relative to the addition of the metal. The ligand, if chiral, can be provided as a racemic mixture or a purified stereoisomer. The ligands are commercially available or can be prepared by the methods similar to processes known in the art.

In some embodiments of the present application, the transition metal catalyst is provided in the reaction in a catalytic amount. In certain embodiments, that amount is in the range of <10 mol %, with respect to the limiting reagent, which may be either the compound of formula (I) or the compound of formula (II), depending upon which reagent is in stoichiometric insufficiency.

In some embodiments of the present application, the reaction is carried out in a solvent which is selected from the group consisting of aromatic hydrocarbons, aliphatic hydrocarbons, alicyclic hydrocarbons, halohydrocarbons, alcohols, ethers, esters, ketones, nitriles and diol derivatives, and ionic liquids such as imidazolium salts.

Exemplary aromatic hydrocarbons that can be used in the present application include, but are not limited to, benzene, toluene, xylene, and the like. Exemplary aliphatic hydrocarbons that can be used in the present application include, but are not limited to, pentane, hexane, heptane, octane, and the like. Exemplary alicyclic hydrocarbons that can be used in the present application include, but are not limited to, cyclohexane, cyclohexanone, methylcyclohexanone, and the like. Exemplary aliphatic hydrocarbons that can be used in the present application include, but are not limited to, pentane, hexane, heptane, octane, and the like. Exemplary halohydrocarbons that can be used in the present application include, but are not limited to, methylene chloride, chloroform, and the like. Exemplary alcohols that can be used in the present application include, but are not limited to, methanol, ethanol, isopropanol, and the like. Exemplary ethers that can be used in the present application include, but are not limited to, diethyl ether, methyl ethyl ether, propyl ether, propylene oxide, and the like. Exemplary esters that can be used in the present application include, but are not limited to, methyl formate, ethyl formate, butyl formate, pentyl formate, methyl acetate, ethyl acetate, propyl acetate, benzyl phenylacetate, and the like. Exemplary ketones that can be used in the present application include, but are not limited to, acetone, methylbutanone, methyl isobutyl ketone, and the like. Exemplary nitriles that can be used in the present application include, but are not limited to, acetonitrile, propionitrile, acrylonitrile, and the like. Exemplary diol derivatives that can be used in the present application include, but are not limited to, ethylene glycol monomethyl ether, ethylene glycol monoethyl ether, ethylene glycol monobutyl ether, and the like.

In some embodiments of the present application, the solvent is an aromatic hydrocarbon. In some embodiments of the present application, the solvent is selected from the group consisting of benzene, toluene and xylene. In some embodiments of the present application, the solvent is toluene.

Alternatively, the reaction can be carried out in the alkene substrates themselves (neat condition). Ionic liquid, such as imidazolium salts, can be also used as reaction medium.

In some embodiments of the present application, the process may be carried out optionally in a buffer to minimize the problems related to isomerization, oligomerization and polymerization. Examples of the buffer which can be used in the present application include but not limited to ammonium salt, phosphorous buffer, carbonates.

In another aspect, the present application is directed to a compound of formula (III)

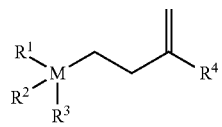

III

M is a metalloid, $R^1$, $R^2$ and $R^3$ are each independently selected from the group consisting of H, alkyl, alkenyl, aryl, arylalkyl, hydroxyl, alkoxyl, aroxyl, halogen, amino, alkylamino, arylamino, mercapto, alkylthio and arylthio, and $R^4$ is alkyl, cycloalkyl, aryl or arylalkyl.

In some embodiments of the present application, M is Si.

In some embodiments of the present application, $R^1$, $R^2$ and $R^3$ are each independently selected from the group consisting of alkyl, aryl and alkoxyl.

The following examples are provided by way of illustration and not by way of limitation.

EXAMPLES

The active catalyst was generated by using a transition metal with a (heterocyclic) carbene ligand and a hydride precursor, with a general structure of [carbene-M-H]X.

The co-dimerization was achieved by adding the corresponding alkenes to the catalyst solution, stirring at room temperature for 24 hrs under nitrogen atmosphere.

A buffer may be used to minimize the problems related to isomerization, oligomerization and polymerization.

Typical procedure for the in situ catalyst generation including:

Under a nitrogen/inert atmosphere, to a solution of a carbene (10 mol %) and $Ni(cod)_2$ (10 mol %) in 2 mL toluene in a typical round bottom flask equipped with a magnetic stir bar, 1-octene (20 mol %), triethylamine (30 mol %), p-anisaldehyde (10 mol %) and silyl triflate (20 mol %) were added sequentially at room temperature. The catalyst was generated after 30 mins of stirring at room temperature using normal bench-top apparatus. In situ catalyst generation can be done alternatively using a compound with a general formula of benzyl or allyl-X to replace the carbonyl compounds, where X equal to leaving group. Also the catalyst could be generated by oxidative addition using the corresponding ionic liquid and $Ni(cod)_2$.

Typical homoallylmetalloid preparation procedure including:

The two different alkene substrates can be added to the catalyst mixture after the catalyst generation. Keep on stirring for another 24 hrs at room temperature and normal pressure on bench top, work up by filtering it through a pad of silica gel and concentrate in vacuum. (e.g. Commercially available dimethylphenylvinylsilane and 1-octene, 100% conversion, quantitative yield (h-t) based on dimethylphenylvinylsilane, with the corresponding homoallylsilane as exclusive isomer).

Following the above general procedures, various organometalloids were synthesized from the corresponding starting materials and the characterization data thereof are provided. In the following Examples, no other co-dimers and silylative coupling products were observed unless otherwise indicated. The yields were based on vinylsilane and average of at least two runs unless otherwise indicated.

Example 1

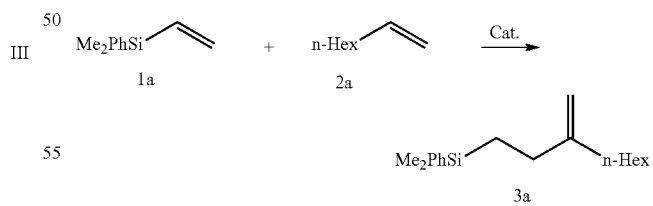

Catalyst generation: $Ni(cod)_2$ and IPr (0.05 mmol, 10 mol % each) were added to an oven-dried test tube equipped with a stir bar in glove box. After sealed with a septum and brought out of the glove box, it was connected to a $N_2$ line. The mixture was dissolved in 2 mL degassed toluene and stirred at room temperature for 1 h. 1-octene (20 mol %), $NEt_3$ (0.15 mmol), p-anisaldehyde (10 mol %), TESOTf (20 mol %) were then added sequentially and stirred 15 mins at room temperature.

Figure 1B:
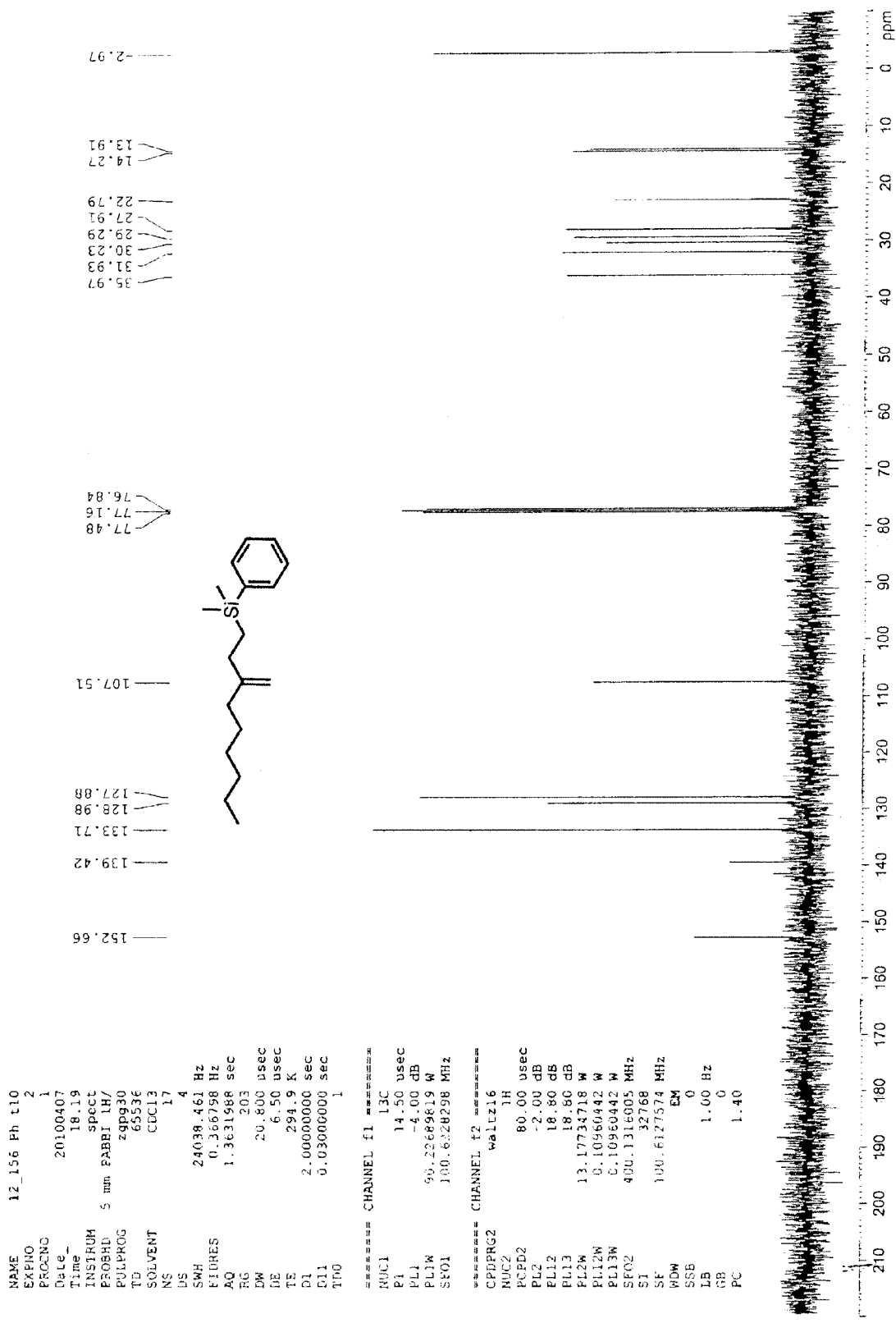

The compound 1a, dimethylphenylvinylsilane (0.5 mmol) and the compound 2a, 1-octene (2.0 mmol) were added to the in situ generated catalyst mixture [(10 mol % "[IPr—Ni—H]OTf") and 0.15 mmol NEt$_3$ in 2.0 mL toluene, see below] at room temperature and stirred for 24 hrs. The desired product 3a was isolated by typical silica gel column chromatography. No vinylsilane self-dimerization products were found in the reaction. Yield of desired product 3a: ≧95%. The $^1$H- and $^{13}$C-NMR spectra of the compound 3a were shown in FIGS. 1A and 1B, respectively.

Example 2

Following the same procedure as in Example 1, but using IMes in place of IPr, product 3a was obtained with a yield of 11%.

Example 3

Following the same procedure as in Example 1, but using PCy$_3$ in place of IPr, product 3a was obtained with a yield of 7%.

Example 4

Following the same procedure as in Example 1, but using THF in place of toluene as the solvent, product 3a was obtained with a yield of ≧95%.

Example 5

Following the same procedure as in Example 1, but at a 2.5 times larger scale, product 3a was obtained with a yield of 84%. When calculated on the basis of vinylsilane conversion, the yield would be 98%.

Example 6

Figure 2A:
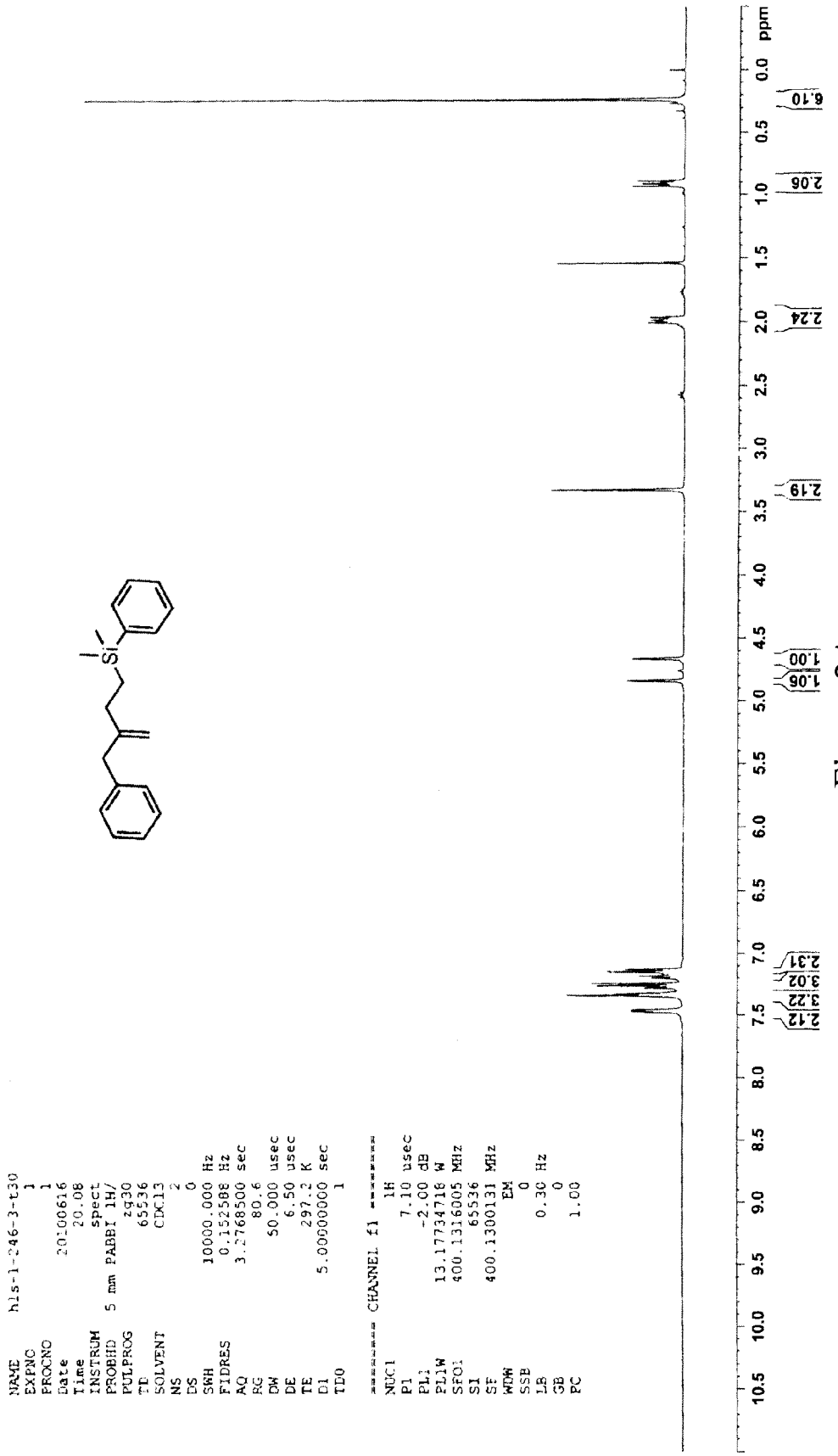
FIGS. 2A and 2B show $^1$H- and $^{13}$C-NMR spectra of the compound 3b.
Figure 2B:
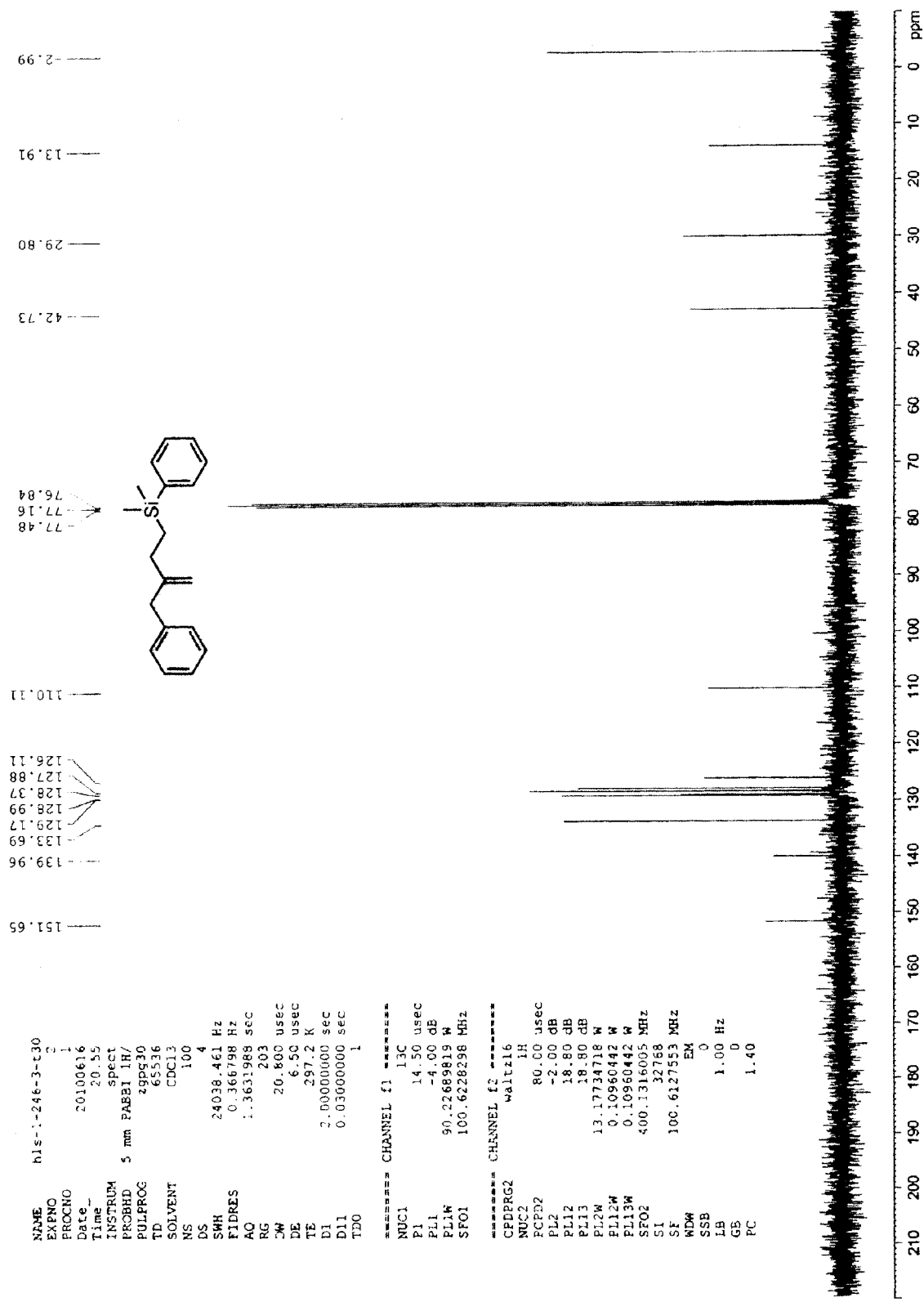

Following the same procedure as in Example 1, but using 3-phenyl-1-propene in place of 1-octene, product 3b was obtained with a yield of ≧95%. The $^1$H- and $^{13}$C-NMR spectra of the compound 3b were shown in FIGS. 2A and 2B, respectively.

Example 7

Figure 3A:
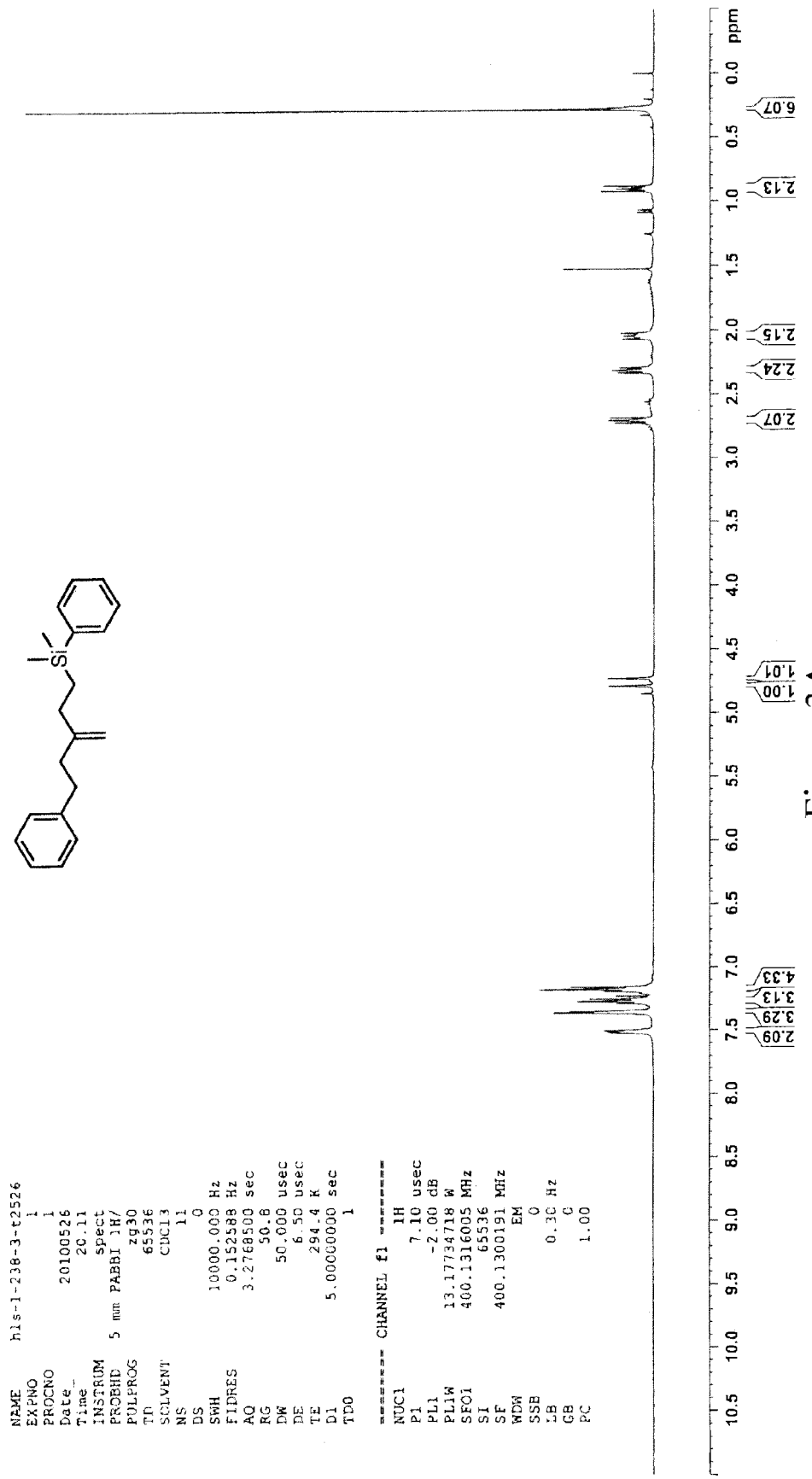
FIGS. 3A and 3B show $^1$H- and $^{13}$C-NMR spectra of the compound 3c.
Figure 3B:
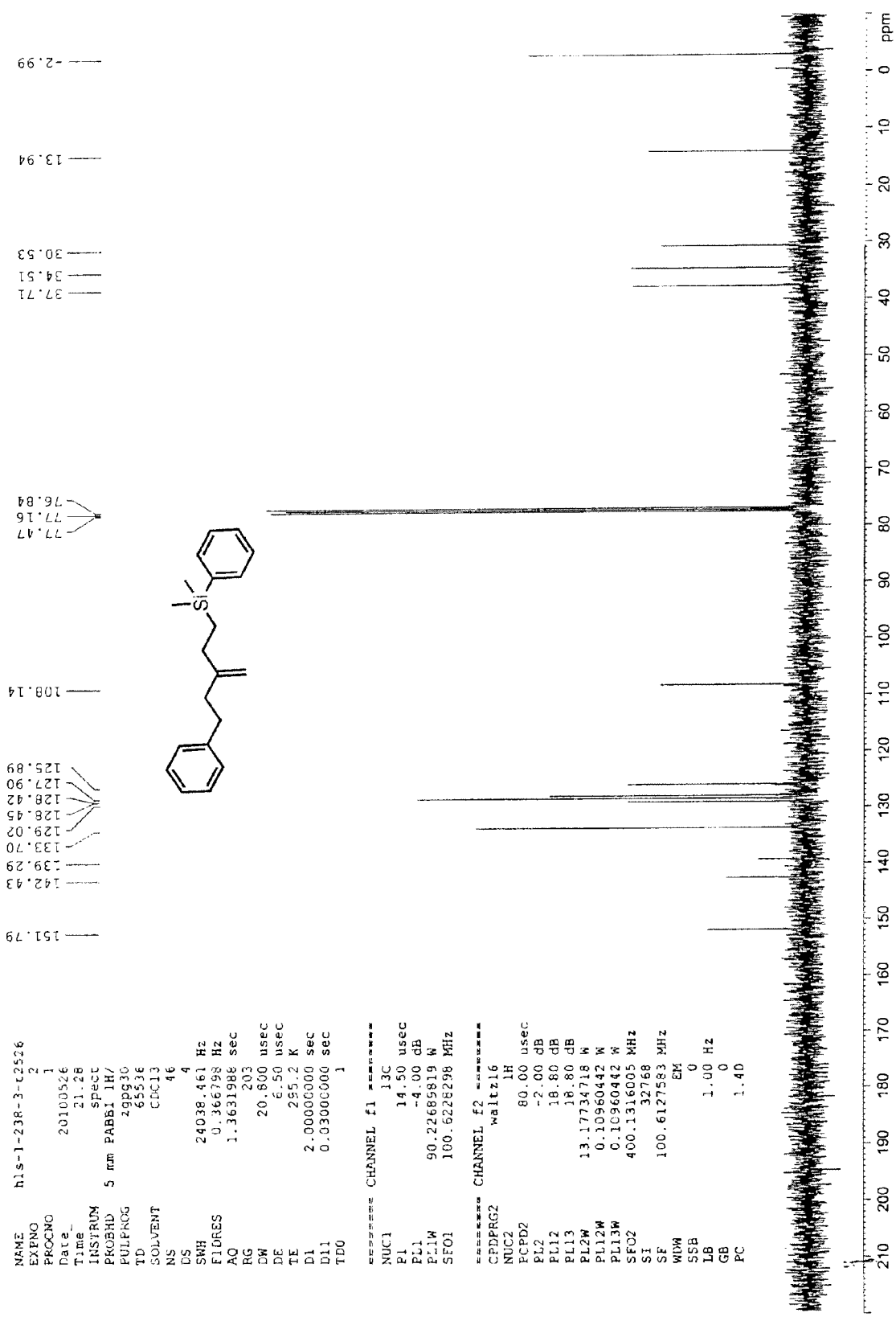

Following the same procedure as in Example 1, but using 4-phenyl-1-butene in place of 1-octene, product 3c was obtained with a yield of 88%. When calculated on the basis of vinylsilane conversion, the yield would be 98%. The $^1$H- and $^{13}$C-NMR spectra of the compound 3c were shown in FIGS. 3A and 3B, respectively.

Example 8

Following the same procedure as in Example 1, but using 11-methoxy-1-undecene in place of 1-octene, product 3d was obtained with a yield of 72%. When calculated on the basis of vinylsilane conversion, the yield would be 95%.

Example 9

Figure 4A:
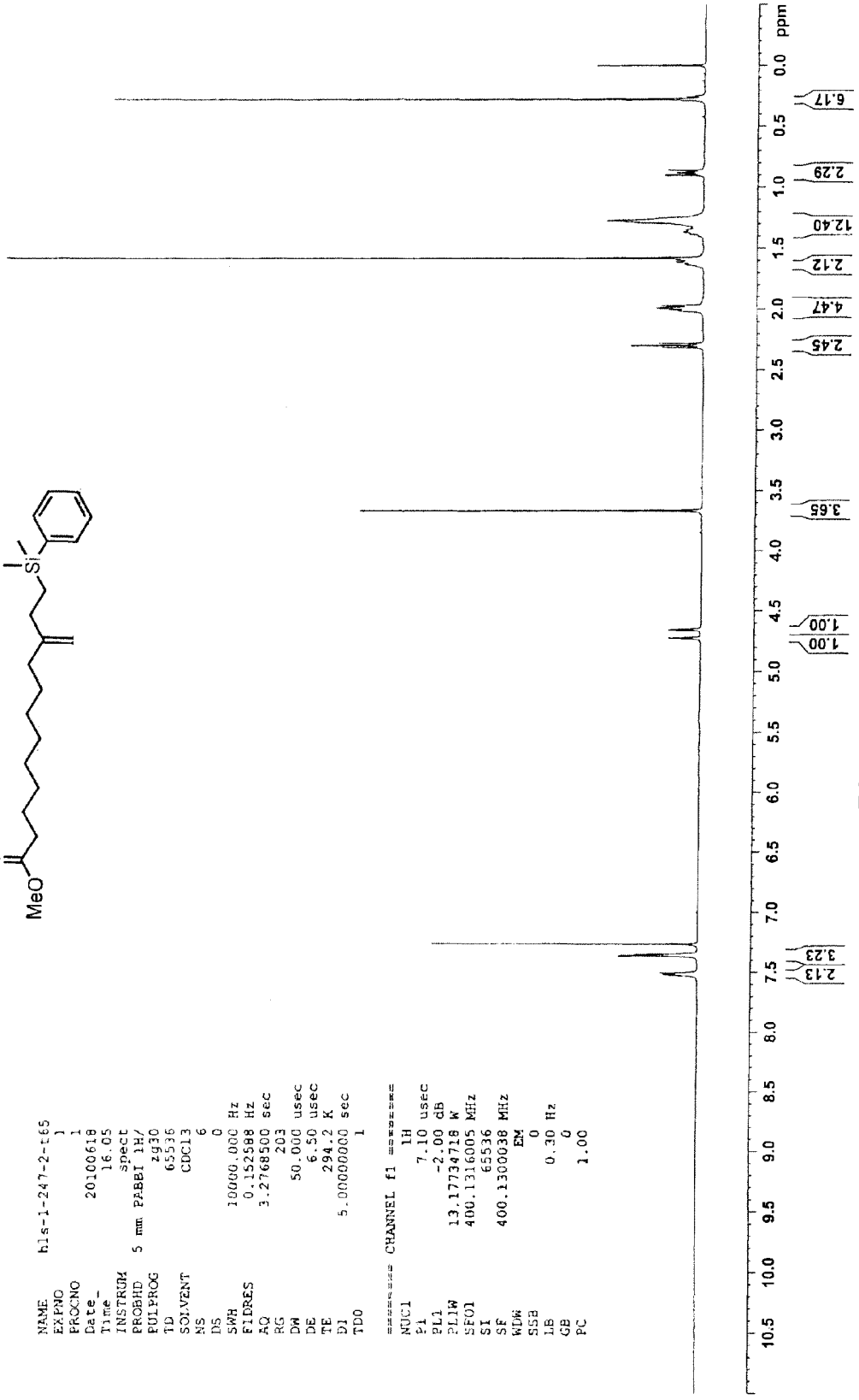
FIGS. 4A and 4B show $^1$H- and $^{13}$C-NMR spectra of the compound 3e.
Figure 4B:
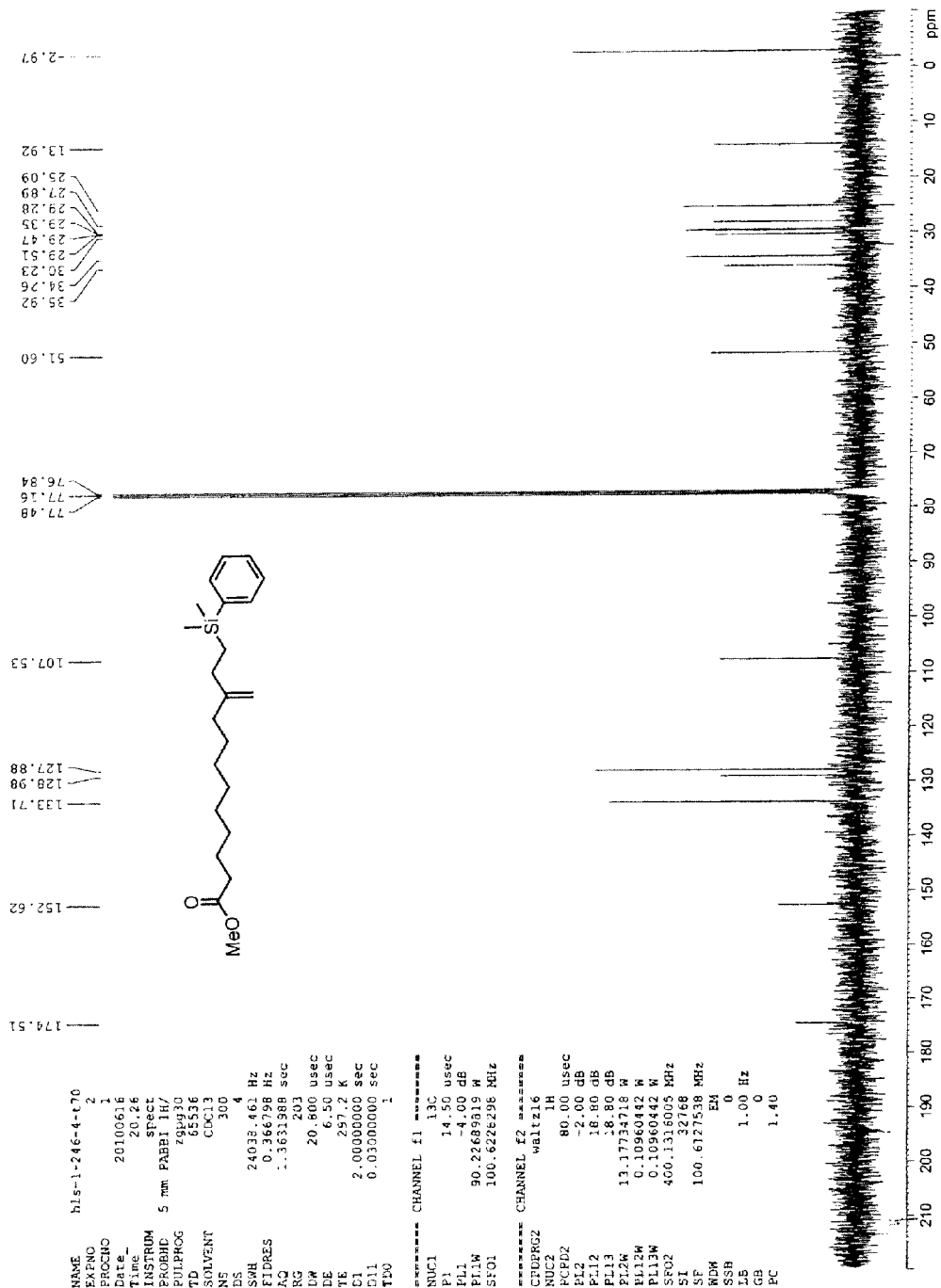

Following the same procedure as in Example 1, but using methyl undecylenate in place of 1-octene, product 3e was obtained with a yield of 80%. When calculated on the basis of vinylsilane conversion, the yield would be 98%. The $^1$H- and $^{13}$C-NMR spectra of compound 3e were shown in FIGS. 4A and 4B, respectively.

Example 10

Following the same procedure as in Example 1, but using cyclohexyl ethene in place of 1-octene, product 3f was obtained with a yield of 8%. When calculated on the basis of vinylsilane conversion, the yield would be 36%.

Example 11

Figure 5A:
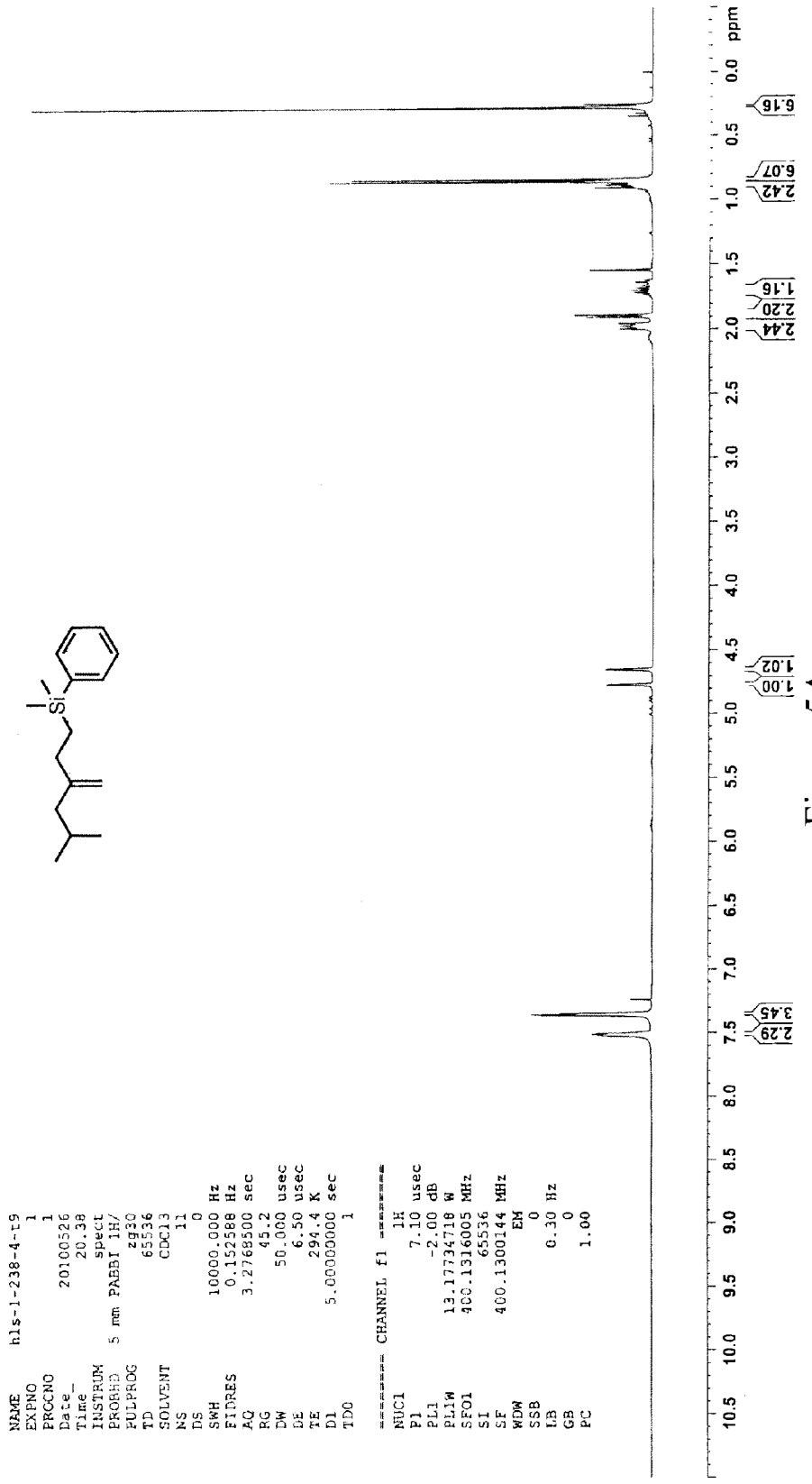
FIGS. 5A and 5B show $^1$H- and $^{13}$C-NMR spectra of the compound 3g.
Figure 5B:
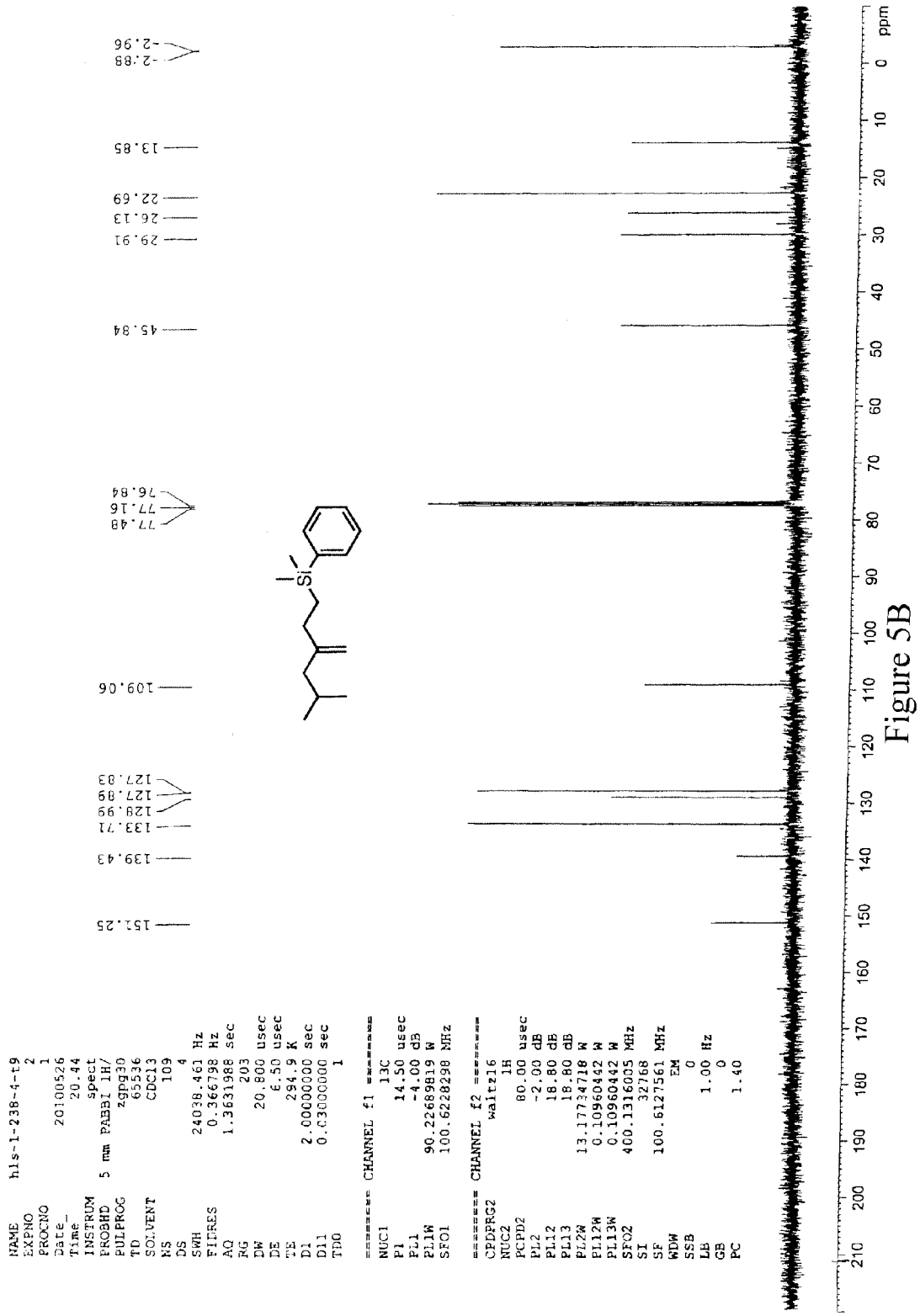

Following the same procedure as in Example 1, but using 4-methyl-1-pentene in place of 1-octene, product 3g was obtained with a yield of 40%. When calculated on the basis of vinylsilane conversion, the yield would be 77%. The $^1$H- and $^{13}$C-NMR spectra of compound 3g were shown in FIGS. 5A and 5B, respectively.

Example 12

Following the same procedure as in Example 1, but using triphenylvinylsilane in place of dimethylphenylvinylsilane, 4-methyl-1-pentene in place of 1-octene, and IMes in place of IPr, product 3h was obtained with a yield of 30%. When calculated on the basis of vinylsilane conversion, the yield would be 88%.

Example 13

Figure 6A:
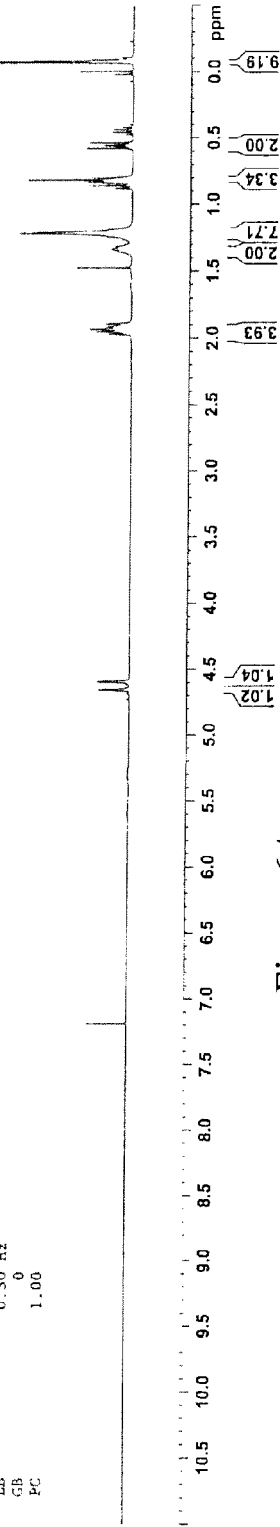
FIGS. 6A and 6B show $^1$H- and $^{13}$C-NMR spectra of the compound 3.
Figure 6B:
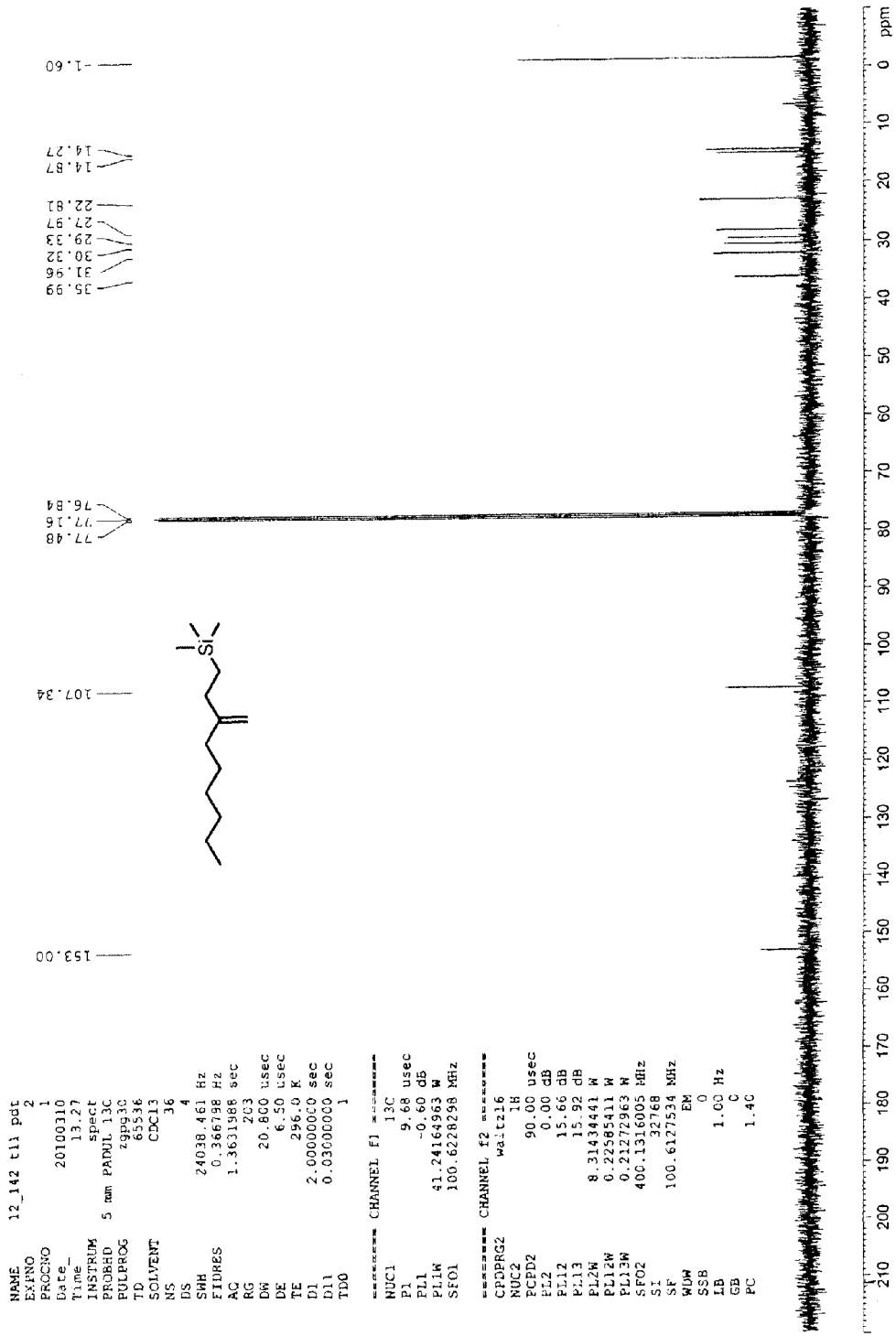

Following the same procedure as in Example 1, but using trimethylvinylsilane in place of dimethylphenylvinylsilane, product 3i was obtained with a yield of 70%. The $^1$H- and $^{13}$C-NMR spectra of the compound 3i were shown in FIGS. 6A and 6B, respectively.

Example 14

Figure 7A:
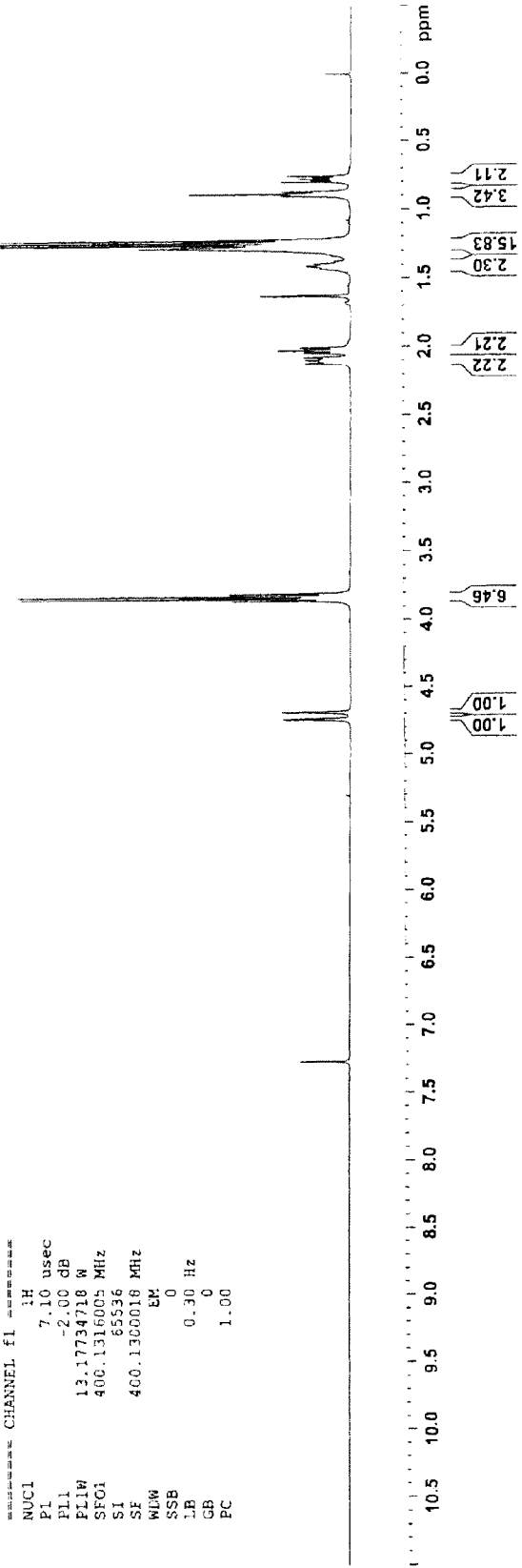
FIGS. 7A and 7B show $^1$H- and $^{13}$C-NMR spectra of the compound 3j.
Figure 7B:
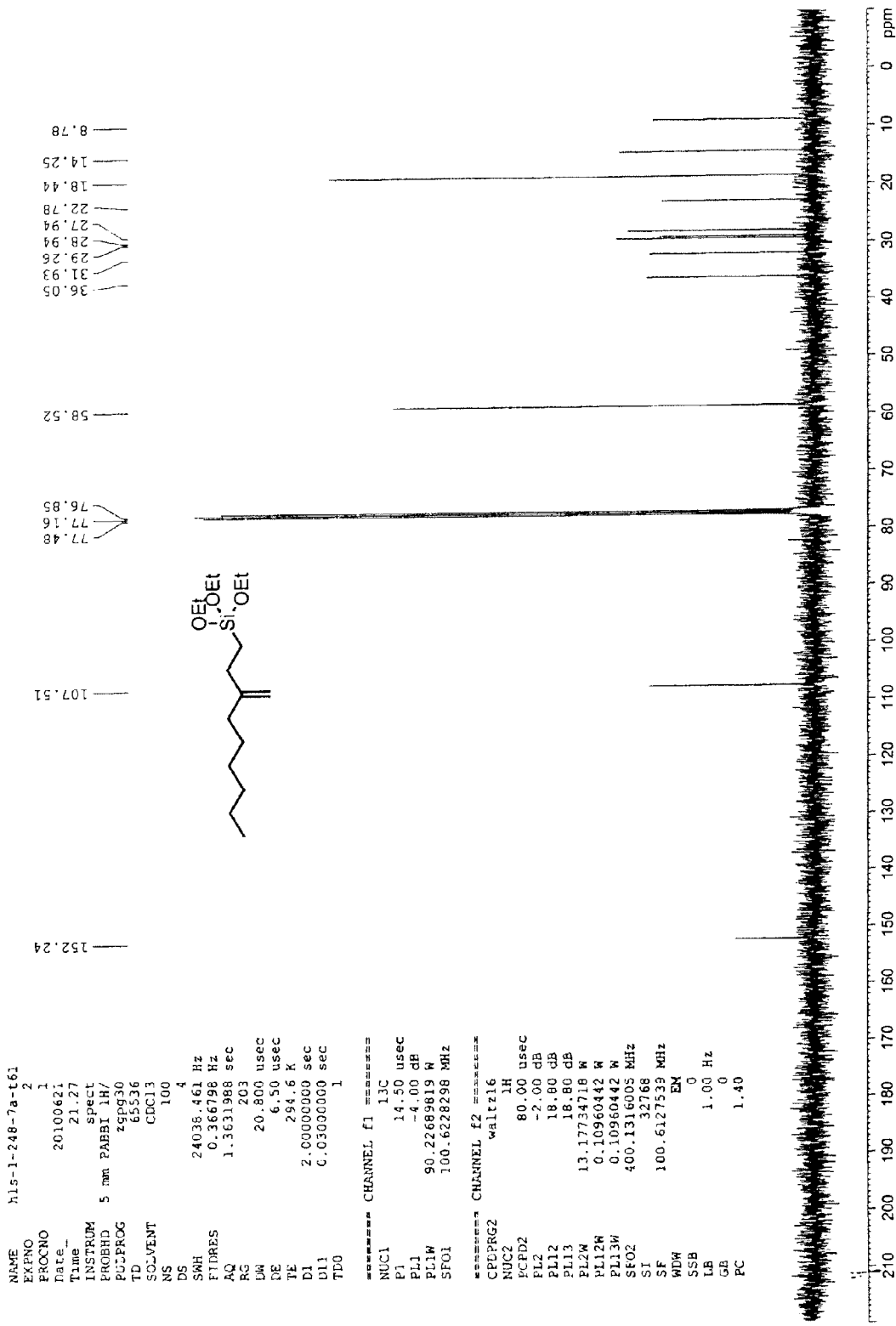

Following the same procedure as in Example 1, but using triethoxyvinylsilane in place of dimethylphenylvinylsilane, product 3j was obtained with a yield of 73%. Meanwhile, a by-product triethoxy(1-hexylvinyl)silane was produced with a yield of 27%. The $^1$H- and $^{13}$C-NMR spectra of compound 3j were shown in FIGS. 7A and 7B, respectively.

Example 15

Figure 8A:
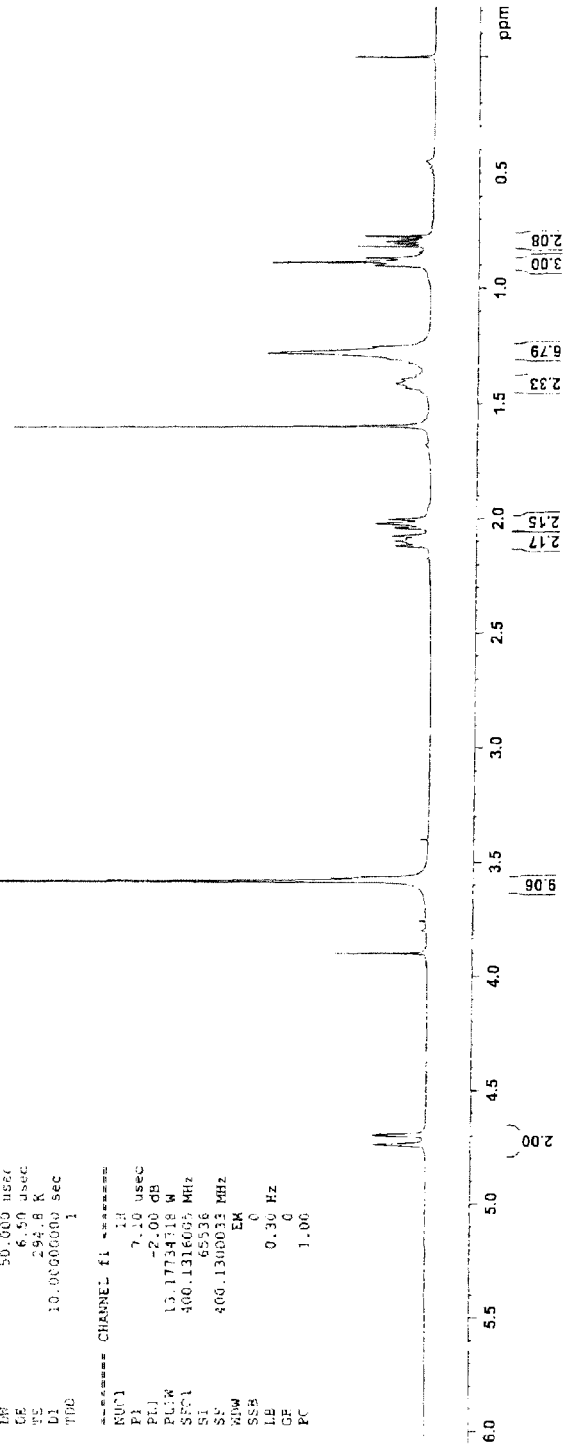
FIGS. 8A and 8B show $^1$H- and $^{13}$C-NMR spectra of the compound 3k.
Figure 8B:
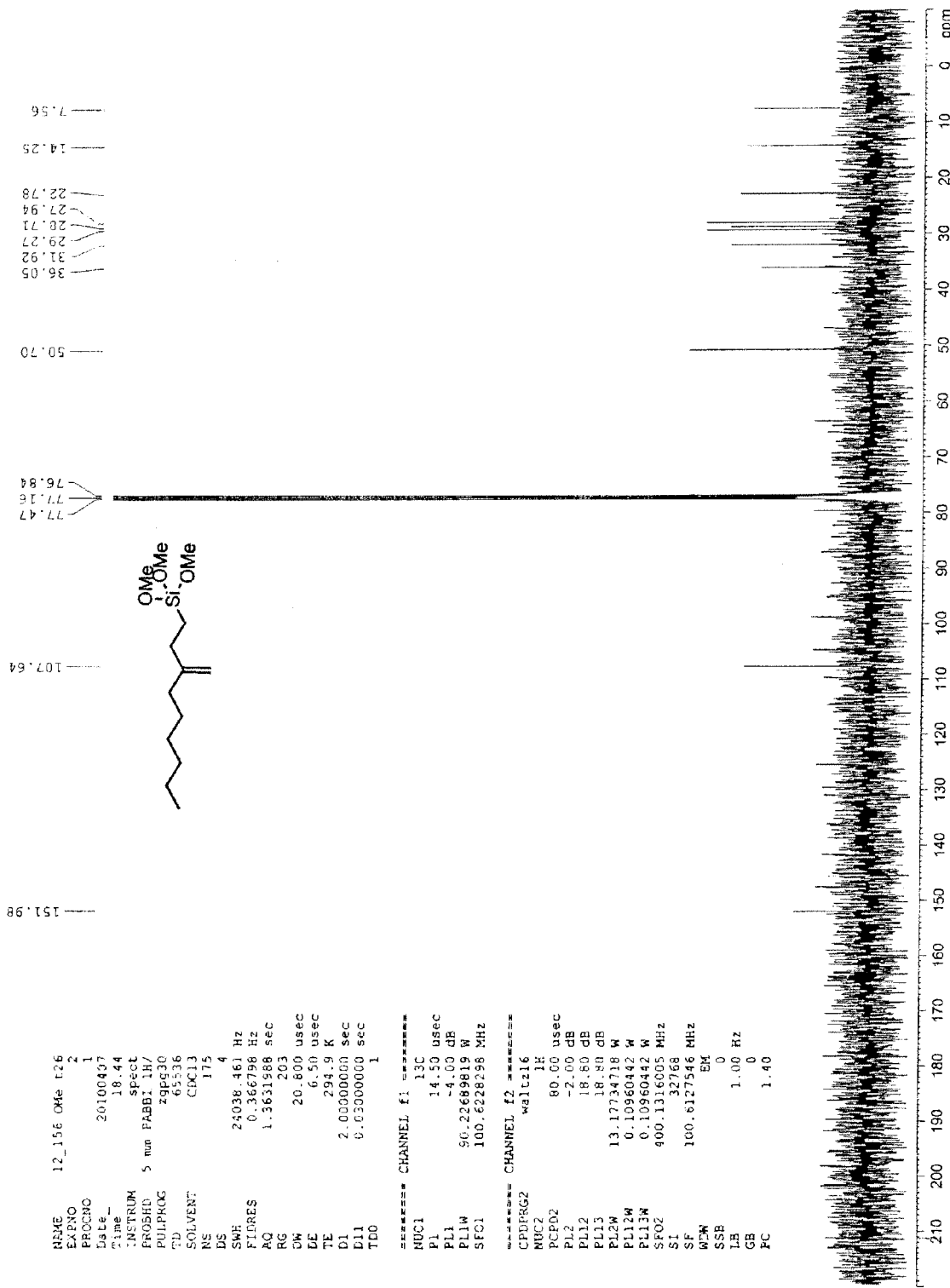

Following the same procedure as in Example 1, but using trimethoxyvinylsilane in place of dimethylphenylvinylsilane, product 3k was obtained with a yield of 50%. Meanwhile, a by-product trimethoxy(1-hexylvinyl)silane was produced with a yield of 24%. The $^1$H- and $^{13}$C-NMR spectra of compound 3k were shown in FIGS. 8A and 8B, respectively.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the application have been described herein for purposes of illustration, various modifications or variations may be made by those skilled in the art without deviating from the spirit and scope of the application.

What is claimed is:

1. A process for preparing a compound of formula (III), comprising reacting a compound of formula (I) with a compound of formula (II) in the presence of a transition metal catalyst or a precursor thereof,

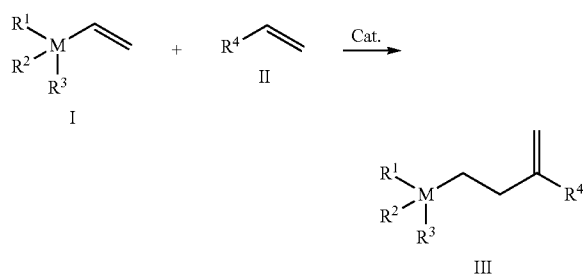

wherein,
M is a metalloid,
R¹, R² and R³ are each independently selected from the group consisting of H, alkyl, alkenyl, aryl, arylalkyl, hydroxyl, alkoxyl, aroxyl, halogen, amino, alkylamino, arylamino, mercapto, alkylthio and arylthio, and
R⁴ is alkyl, cycloalkyl, aryl or arylalkyl.

2. The process of claim 1, wherein M is Si.

3. The process of claim 1, wherein R¹, R² and R³ are each independently selected from the group consisting of alkyl, aryl and alkoxyl.

4. The process of claim 1, wherein the compound of formula (I) is selected from the group consisting of trimethylvinylsilane, dimethylphenylvinylsilane, trimethoxyvinylsilane, triethoxyvinylsilane and triphenylvinylsilane.

5. The process of claim 1, wherein the compound of formula (II) is selected from the group consisting of straight chain monoenes, branched chain monoenes, aromatic alkenes, and their substituted derivatives.

6. The process of claim 5, wherein the straight chain monoene is selected from the group consisting of 1-hexene and 1-octene.

7. The process of claim 5, wherein the branched chain monoene is selected from the group consisting of vinylcyclohexane and 4-methyl-1-pentene.

8. The process of claim 5, wherein the aromatic alkene is selected from the group consisting of styrene and allylbenzene.

9. The process of claim 1, wherein the transition metal is selected from Groups 3 to 12 of the Periodic Table of Elements.

10. The process of claim 1, wherein the transition metal is selected from Group 10 of the Periodic Table of Elements.

11. The process of claim 10, wherein the transition metal is Ni.

12. The process of claim 1, wherein the transition metal catalyst comprises a ligand which is selected from the group consisting of carbenes, heterocyclic carbenes, biscarbenes, bisheterocyclic carbenes, phosphines, amines, imines, arsines and derivatives thereof.

13. The process of claim 12, wherein the ligand or metal bears a weakly or non-nucleophilic stabilizing ion which is selected from the group consisting of halogen, sulfonates, and phosphonates.

14. The process of claim 12, wherein the ligand is chiral and is provided as a racemic mixture or a purified stereoisomer.

15. The process of claim 1, wherein the amount of the transition metal is <10 mol %, with respect to a limiting reagent, which is either the compound of formula (I) or the compound of formula (II), depending upon which reagent is in stoichiometric insufficiency.

16. The process of claim 1, wherein the process is carried out in a solvent which is selected from the group consisting of aromatic hydrocarbons, aliphatic hydrocarbons, alicyclic hydrocarbons, halohydrocarbons, alcohols, ethers, esters, ketones, nitriles and diol derivatives, and ionic liquids.

17. The process of claim 16, wherein the solvent is selected from the group consisting of benzene, toluene, and xylene.

18. The process of claim 16, wherein the solvent is toluene.

19. The process of claim 1, wherein the process is carried out in a buffer.

* * * * *